(12) United States Patent
Matioc

(10) Patent No.: US 8,640,692 B2
(45) Date of Patent: Feb. 4, 2014

(54) OROPHARYNGEAL DEVICE FOR ASSISTING ORAL VENTILATION OF A PATIENT

(76) Inventor: Adrian A. Matioc, Fitchburg, WI (US)

(*) Notice: Subject to any disclaimer, the term of this patent is extended or adjusted under 35 U.S.C. 154(b) by 559 days.

(21) Appl. No.: 12/693,920

(22) Filed: Jan. 26, 2010

(65) Prior Publication Data

US 2010/0199998 A1 Aug. 12, 2010

Related U.S. Application Data

(60) Provisional application No. 61/151,239, filed on Feb. 10, 2009.

(51) Int. Cl.
*A61M 16/00* (2006.01)
*A62B 9/06* (2006.01)

(52) U.S. Cl.
USPC .................................. 128/200.26; 128/207.14

(58) Field of Classification Search
USPC ......................................... 128/200.26, 207.14
See application file for complete search history.

(56) References Cited

U.S. PATENT DOCUMENTS

| 2,127,215 A | 8/1938 | Gwathmey |
| 2,599,521 A | 6/1952 | Berman |
| 3,306,298 A * | 2/1967 | Raimo ..................... 128/207.14 |
| 3,568,680 A | 3/1971 | Raimo |
| 3,576,187 A | 4/1971 | Oddera |
| 3,756,244 A | 9/1973 | Kinnear et al. |
| 3,908,665 A | 9/1975 | Moses |
| 3,930,507 A | 1/1976 | Berman |
| 4,112,936 A | 9/1978 | Blachly |
| 4,356,821 A | 11/1982 | Rind |
| 4,363,320 A | 12/1982 | Kossove |
| 4,553,540 A | 11/1985 | Straith |
| 4,919,126 A | 4/1990 | Baildon |
| 5,024,218 A | 6/1991 | Ovassapian et al. |
| 5,443,063 A | 8/1995 | Greenberg |
| 5,590,643 A * | 1/1997 | Flam ......................... 128/200.26 |
| 5,653,229 A * | 8/1997 | Greenberg .............. 128/207.15 |
| 5,740,791 A | 4/1998 | Aves |
| 6,196,224 B1 | 3/2001 | Alfery |
| 6,517,549 B1 * | 2/2003 | Dennis ........................ 606/108 |
| 6,606,991 B2 | 8/2003 | Chou |
| 6,679,901 B1 | 1/2004 | Takuma |
| 2008/0230054 A1 * | 9/2008 | Prineas .................... 128/200.26 |
| 2009/0050161 A1 * | 2/2009 | Burdumy ..................... 128/861 |

OTHER PUBLICATIONS

Boidin, M.P., Airway Patency in the Unconscious Patient. British Journal of Anaesthesia. 1985; 57: 306-310.

* cited by examiner

*Primary Examiner* — Nicholas Lucchesi
*Assistant Examiner* — Leah Stohr
(74) *Attorney, Agent, or Firm* — Quarles & Brady LLP

(57) ABSTRACT

An oropharyngeal device for assisting oral ventilation of a patient is disclosed. The device comprises a pharyngeal section configured to engage the tongue of the patient and a bite block connected to the pharyngeal section. The bite block includes a proximate maxillary surface configured to engage at least a portion of the maxilla of the patient. The bite block further includes a maxillary flange adjacent the proximate maxillary surface that is configured to engage the upper lip of the patent. The bite block further includes a mandibular surface opposite the proximate maxillary surface. At least a portion of the mandibular surface opposite the maxillary flange is configured to engage at least a portion of the mandible of the patient.

23 Claims, 12 Drawing Sheets

OROPHARYNGEAL DEVICE FOR ASSISTING ORAL VENTILATION OF A PATIENT

CROSS-REFERENCE TO RELATED APPLICATION

This application claims the benefit of U.S. Provisional Patent Application No. 61/151,239 filed Feb. 10, 2009, the disclosure of which is hereby incorporated by reference in its entirety.

STATEMENT REGARDING FEDERALLY SPONSORED RESEARCH OR DEVELOPMENT

Not applicable.

FIELD OF THE INVENTION

The invention relates to medical devices suited to airway management through the mouth of a patient in a supine position.

BACKGROUND OF THE INVENTION

In the areas of anesthesiology, emergency medicine, critical care, and resuscitation as well as other medical areas, one practitioner typically monitors ventilation, and provides airway management, for an unconscious patient. Airway management commonly involves ventilating a patient by holding a face mask over the patient's mouth and delivering oxygen with positive pressure. Such practices, while typically effective, can fail because the airway passages through which air may be drawn to the patient's lungs can easily become obstructed when the patient lies in a supine position. The airways are typically obstructed because the mandible tends to move downward relative to the maxilla, and the soft tissues in the throat tend to relax. As a result, contact of the tongue, the soft palate, and the epiglottis with the pharynx may occur which prevents air in the mouth and nose from reaching the lungs. Therefore, during positive pressure ventilation a practitioner must appropriately relieve the obstruction generated by the soft throat tissues to provide a patent airway to the lungs.

Practitioners often use a device, typically referred to as an oropharyngeal airway, in conjunction with a face mask to support positive pressure ventilation. The oropharyngeal airway is shaped to open the airway between the tongue and the pharynx within a patient's throat. Referring to FIG. 1, a prior art oropharyngeal airway 30 is shown positioned in the mouth and throat of an unconscious patient 10. The oropharyngeal airway 30 is typically a single piece device formed by a generally rigid plastic material. The oropharyngeal airway 30 includes symmetrical mandibular and maxillary flanges 32 and 34 that engage the lower and upper lips 12 and 14, respectively, to stabilize the device and to prevent overinsertion, a bite block 36 that engages and separates the lower and upper teeth 16 and 18, and a pharyngeal section 38 that lifts the tongue 20 off the pharynx 22 and opens the airway. The pharyngeal section 38 is designed to closely match the shape of the tongue 20 and other tissues and, as shown in FIG. 1, properly engages the tongue 20 when the mandibular and maxillary flanges 32 and 34 engage the lips 12 and 14. The pharyngeal section 38 also typically includes an internal channel 40, or alternatively, the oropharyngeal airway 30 is I-shaped to provide a passageway through which air may pass to the lungs. The oropharyngeal airway 30, while effective for removing obstructions in some situations, has several drawbacks. For example, the pharyngeal section 38 only lifts the tongue 20 off the pharynx 22, and the epiglottis 24 may contact the pharynx 22 and obstruct the airway.

Practitioners often use a technique in which the mandible is advanced to move the epiglottis and the base of the tongue in a supine unconscious patient and clear the obstruction in the airway. One such technique, known as the jaw thrust, simply involves lifting or advancing the mandible upward relative to the maxilla. Another technique, known as the chin lift/head extension, involves rotating the head backwards while pulling the chin up. Another technique, known as the triple airway maneuver, is used by practitioners and involves three steps: lifting the mandible upward, opening the mouth, and rotating the top of the head backwards. The triple airway maneuver combines the motions of jaw thrust and chin lift/head extension techniques, and therefore, may be simply described as jaw thrust, mouth open, and head extension. Techniques such as the triple airway maneuver are recommended in emergency procedures, and as a result, are well-known by trained medical practitioners. However, the triple airway maneuver is complex and is not applied with a face mask to support positive pressure ventilation. In addition, the triple airway maneuver cannot be properly used with a conventional oropharyngeal airway due to the shape of the device and the symmetrical flanges that limit the advancement of the mandible to position the inferior teeth anterior to the superior teeth.

In addition, use of the triple airway maneuver is currently limited to situations in which two practitioners are available to ventilate the patient. Two practitioners are required because one of the practitioners must perform the triple airway maneuver and then hold the patient in a ventilation position using both hands. The other practitioner then ventilates the patient by squeezing a self-inflatable resuscitator bag. Two practitioners may be available for planned treatments, but in most cases, such as emergent and rescue situations, typically only a single practitioner is present.

Considering the limitations of previous designs, it would be desirable to have an oropharyngeal airway that may be used in conjunction with techniques such as the triple airway maneuver and face mask ventilation to ensure proper ventilation of a patient. It would also be desirable to have an oropharyngeal airway that permits a single practitioner to apply the aforementioned techniques.

SUMMARY OF THE INVENTION

In one aspect, the present invention provides an oropharyngeal device for assisting oral ventilation of a patient. The device comprises a pharyngeal section configured to engage the tongue of the patient and a bite block connected to the pharyngeal section. The bite block includes a proximate maxillary surface configured to engage at least a portion of the maxilla of the patient. The bite block further includes a maxillary flange adjacent the proximate maxillary surface that is configured to engage the upper lip of the patent. The bite block further includes a mandibular surface opposite the proximate maxillary surface. At least a portion of the mandibular surface opposite the maxillary flange is configured to engage at least a portion of the mandible of the patient.

In another aspect, the oropharyngeal device comprises a pharyngeal section configured to engage the tongue of the patient and a bite block connected to the pharyngeal section. The bite block includes a distal end opposite the pharyngeal portion and a maxillary flange offset from the distal end towards the pharyngeal section. The maxillary flange is configured to engage the upper lip of the patent and includes a proximal surface generally facing the pharyngeal portion and a distal surface generally facing away from the pharyngeal portion. The bite block further includes a mandibular surface configured to engage at least a portion of the mandible of the patient and a proximate maxillary surface opposite the mandibular surface and adjacent the proximal surface of the maxillary flange. The proximate maxillary surface is configured to engage at least a portion of the maxilla of the patient. The bite block further includes a distal maxillary surface opposite the mandibular surface and adjacent the distal surface of the maxillary flange.

In yet another aspect, the present invention provides a method of treating a patient in a supine position, comprising the steps of: inserting an oropharyngeal device into the throat of the patient. The oropharyngeal device comprises a proximate maxillary surface, a maxillary flange adjacent the proximate maxillary surface, a mandibular surface opposite the proximate maxillary surface, and at least a portion of the mandibular surface opposite the maxillary flange. The device further comprises a pharyngeal section adjacent the proximate maxillary surface and the mandibular surface. The method further includes the steps of: engaging the pharyngeal section with the tongue of the patient, engaging the maxillary flange with at least a portion of the maxilla of the patient, applying a jaw thrust maneuver to advance the mandible of the patient to a prognathic position past a normal position of the mandible relative to the maxilla, and holding the mandible in the prognathic position by engaging at least a portion of the mandible with the portion of the mandibular surface opposite the maxillary flange.

The foregoing and other advantages of the invention will appear in the detailed description that follows. In the description, reference is made to the accompanying drawings that illustrate a preferred embodiment of the invention.

BRIEF DESCRIPTION OF THE DRAWINGS

The invention will hereafter be described with reference to the accompanying drawings, wherein like reference numerals denote like elements, and.

DETAILED DESCRIPTION OF THE PREFERRED EMBODIMENT

Figure 1:
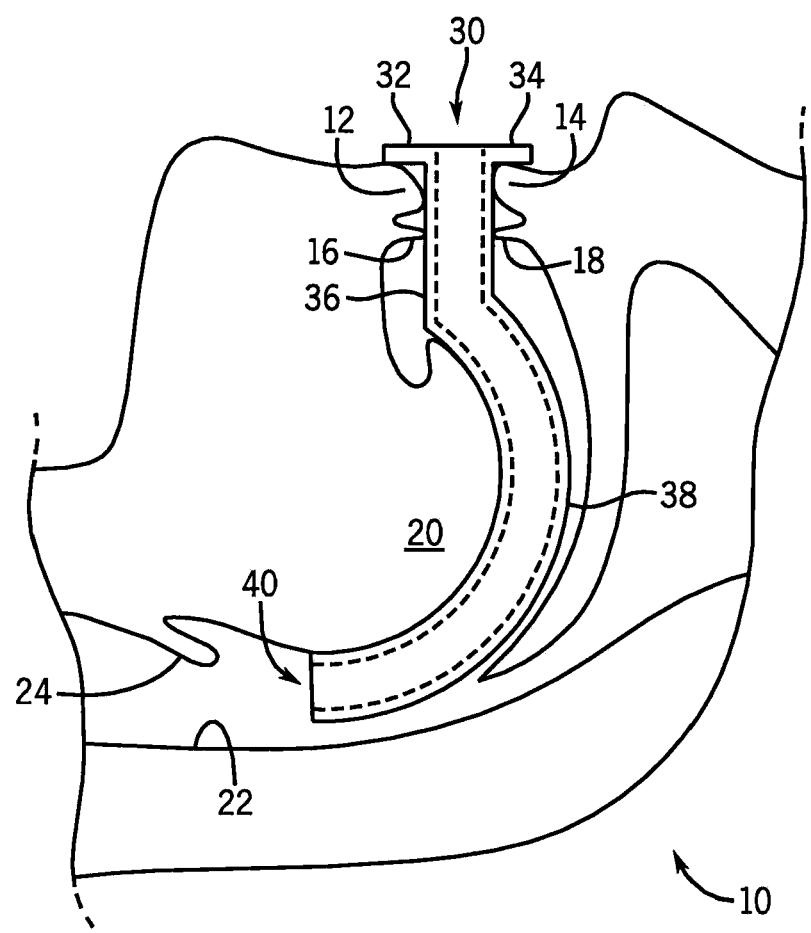
FIG. 1 is a side elevation view of a prior art oropharyngeal airway in a patient's mouth.

Referring to FIGS. 2-7, the present invention provides an oropharyngeal airway 60 for ventilation through the mouth of an unconscious patient in a supine position. The oropharyngeal airway 60 may advantageously be used with recommended techniques, such as the triple airway maneuver, to clear an obstruction of the soft tissues (the soft palate, the base of the tongue and the epiglottis) and the pharynx. The oropharyngeal airway 60 may also be advantageously used with a face mask to ensure proper ventilation of the patient. In general, the oropharyngeal airway 60 includes a proximal section 62 that remains near the teeth and a pharyngeal or distal section 64 that engages the tongue. The proximal section 62 and the pharyngeal section 64 may be made of a single piece of a suitable plastic material or any other suitable material provided that the oropharyngeal airway 60 is sufficiently rigid to maintain its general shape when placed in the mouth and throat of the patient.

The proximal section 62 includes a bite block 66 that has a generally hollow box shape and engages the patient's teeth. The bite block 66 includes an upper or proximate maxillary surface 68 and a lower or mandibular surface 70 opposite the proximate maxillary surface 68. Lateral side surfaces 72 and 74 are disposed between the proximate maxillary and mandibular surfaces 68 and 70. A proximal end 76 and a distal end 78 disposed between the proximate maxillary and mandibular surfaces 68 and 70 are open and permit the bite block 66 to partially define an internal channel 80 through which air, a fiber-optic bronchoscope, a suction tube, an airway exchange catheter, an endotracheal tube or the like may pass.

Figure 2:
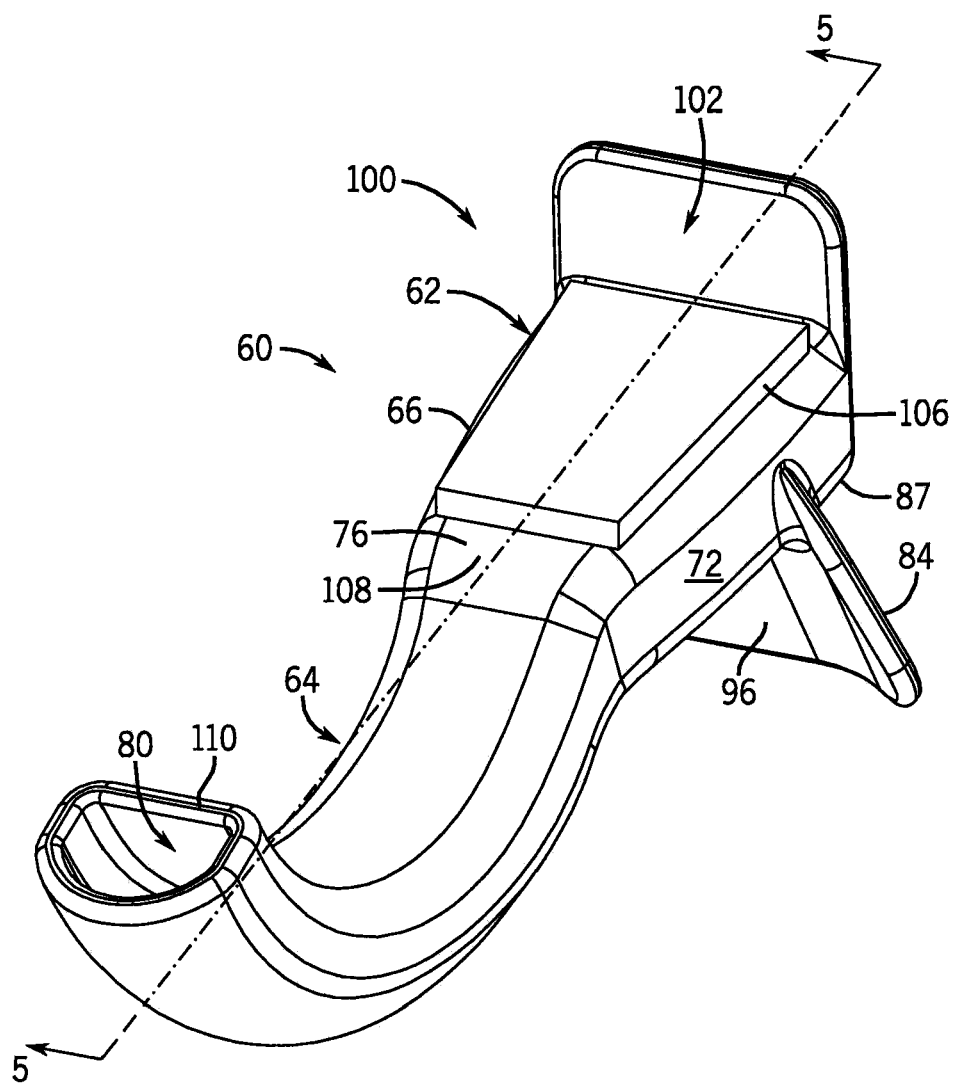
FIG. 2 is a perspective view of an embodiment of an oropharyngeal airway of the present invention.
Figure 5:
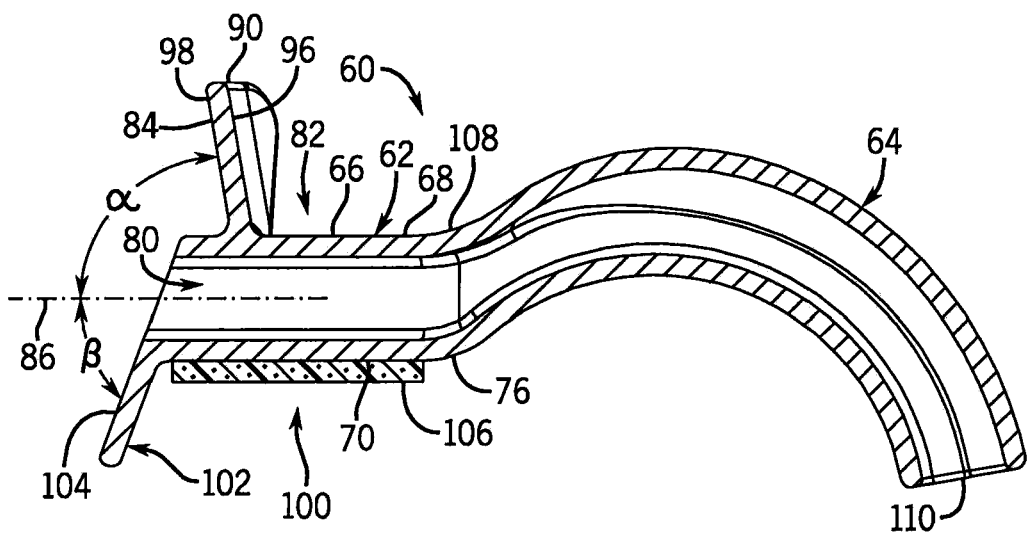
FIG. 5 is a cross-sectional elevation view taken along line 5-5 of FIG. 2.
Figure 6:
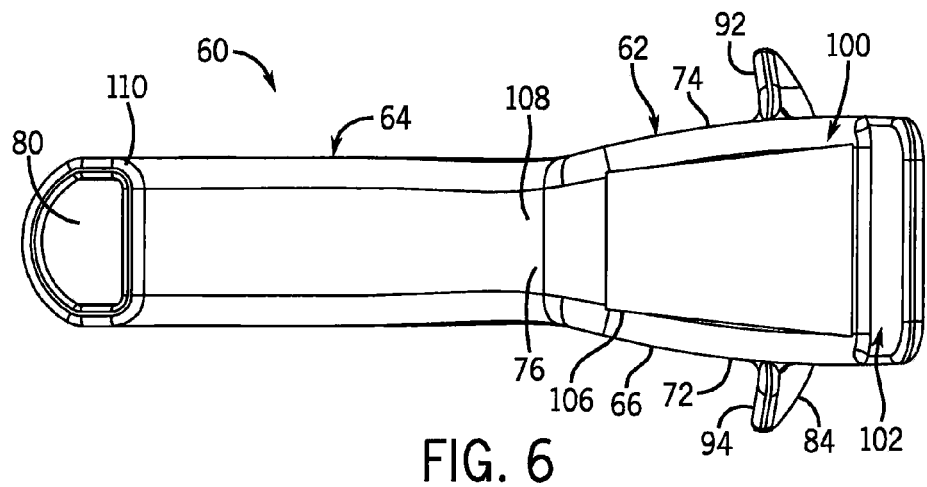
FIG. 6 is an anterior view of the oropharyngeal airway of FIG. 2.

As mostly easily seen in FIGS. 2, 5, and 6, the bite block 66 is generally wider than the pharyngeal section 64. That is, the bite block 66 has a dimension between the lateral side surfaces 72 and 74 that is greater than a dimension of the pharyngeal section 64 between the lateral side surfaces 72 and 74. In addition, the lateral side surfaces 72 and 74 preferably taper outwardly from the proximal end 76 to the distal end 78 to form a generally trapezoidal bite block 66. The width of the bite block 66 and the generally trapezoidal shape, if included, advantageously provide a larger contact surface for the mandible. The generally trapezoidal shape also provides a relatively bulky design that may be effectively used with toothless patients and patients with dentures. That is, the large bite block 66 is relatively stable and appropriate for use with patients that have large mouths without teeth. However, it should be understood that the oropharyngeal airway 60 is also effectively used with patients that have teeth.

Referring again to FIGS. 2-7, a maxillary section 82 of the proximal section 62 includes a maxillary flange 84 that extends outwardly adjacent the proximate maxillary surface 68 and from the lateral side surfaces 72 and 74 and engages the patient's upper lip to stabilize the device 60. The maxillary flange 84 extends outwardly and generally away from the pharyngeal section 64 at an angle α relative to a longitudinal axis 86 (FIGS. 4 and 5) defined by a direction in which air flows through the internal channel 80. The angle α is preferably in the range of about 75 to 80 degrees, but it is also contemplated that the angle α may be up to 90 degrees. In addition, the maxillary flange 84 extends outwardly adjacent the proximate maxillary surface 68 at a position spaced apart from the distal end 78 of the bite block 66, thereby defining a distal maxillary surface 87 adjacent the distal end 78.

Figure 3:
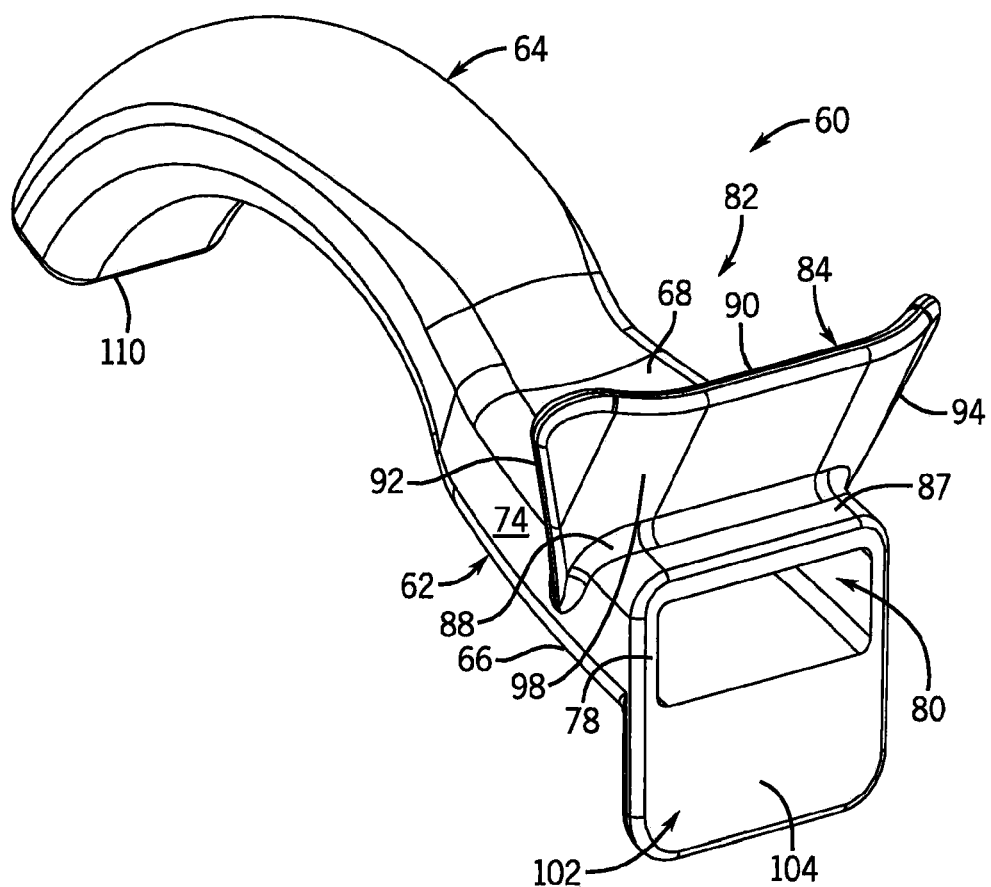
FIG. 3 is a perspective view of the oropharyngeal airway of FIG. 2 viewed from a different angle than FIG. 2.
Figure 4:
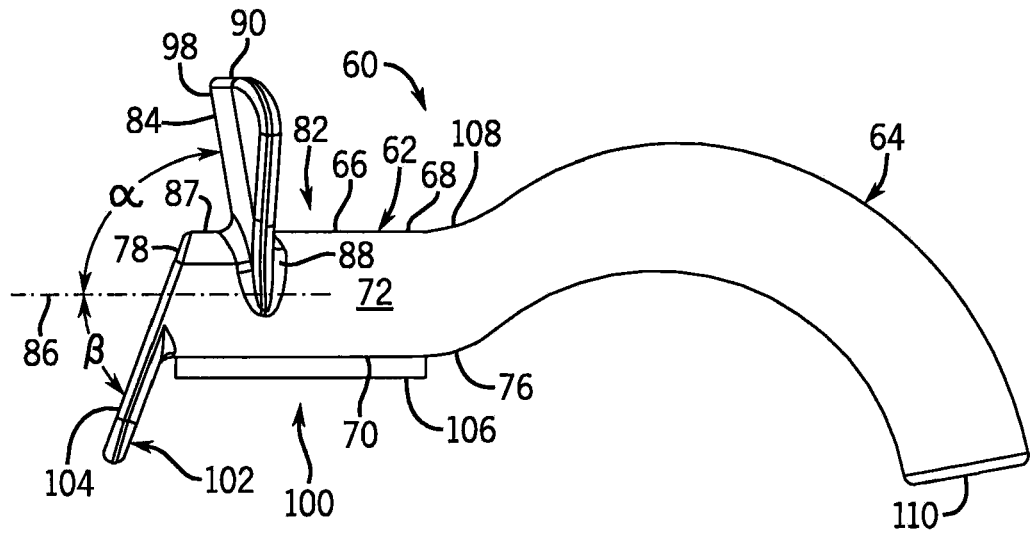
FIG. 4 is a side elevation view of the oropharyngeal airway of FIG. 2.
Figure 7:
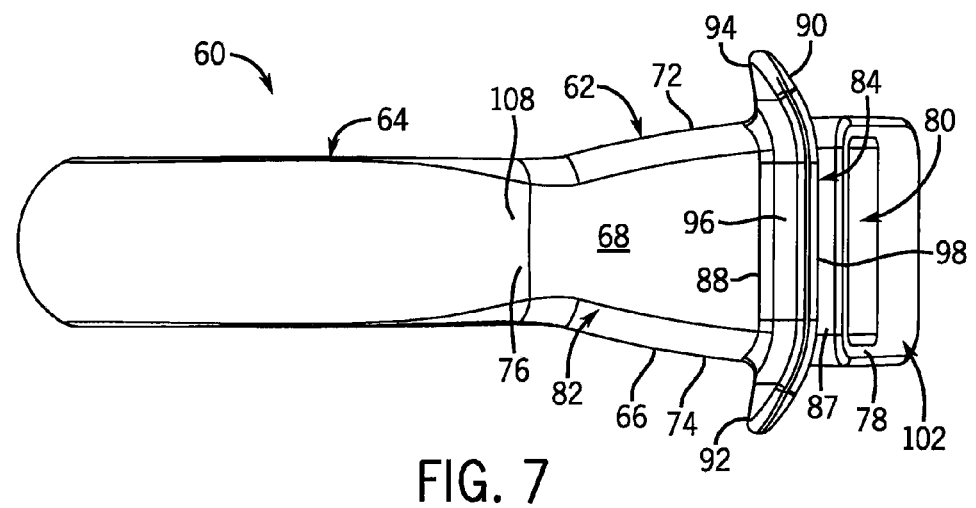
FIG. 7 is a posterior view of the oropharyngeal airway of FIG. 2.
Figure 8:
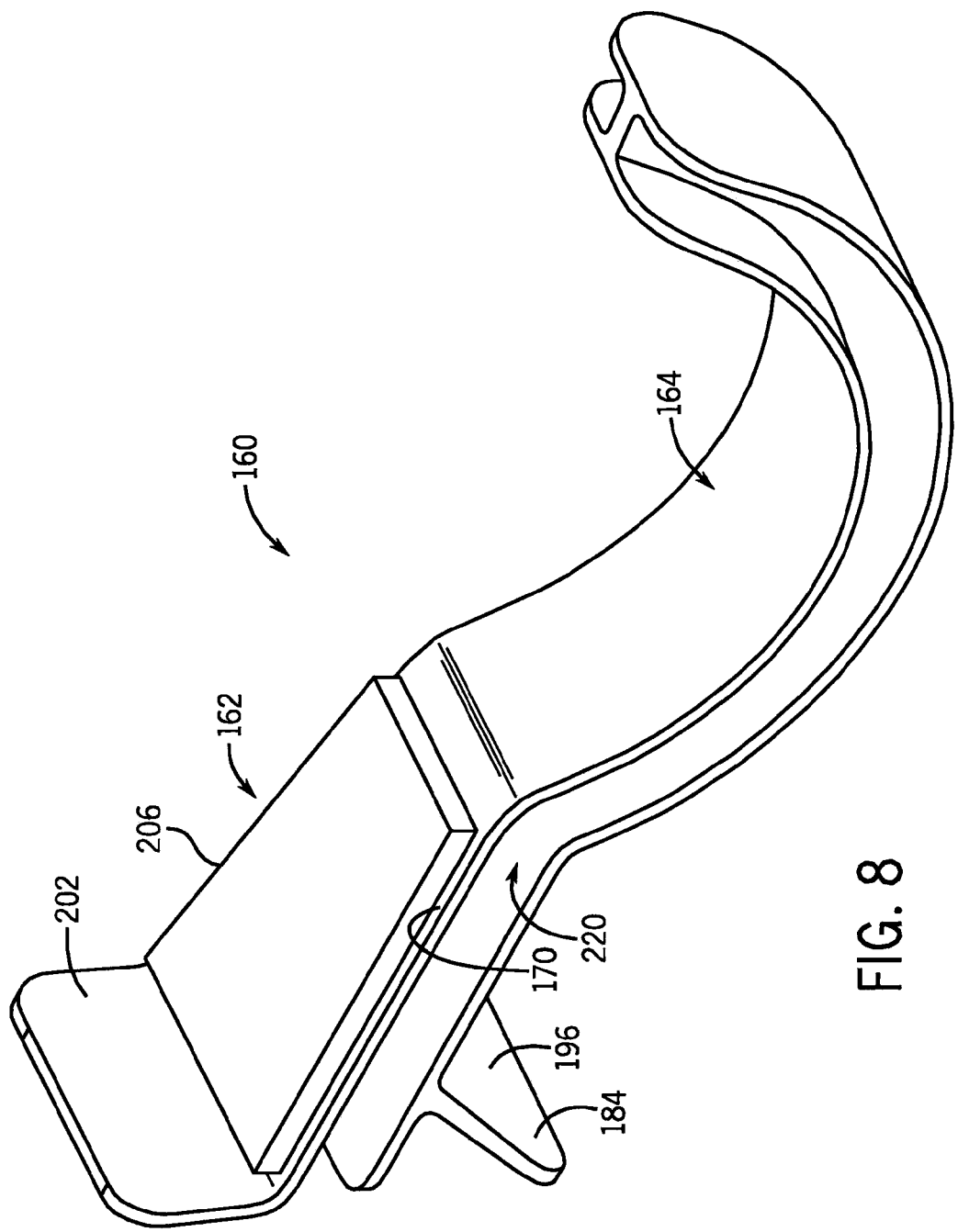
FIG. 8 is a perspective view of a second embodiment of an oropharyngeal airway of the present invention.
Figure 9:
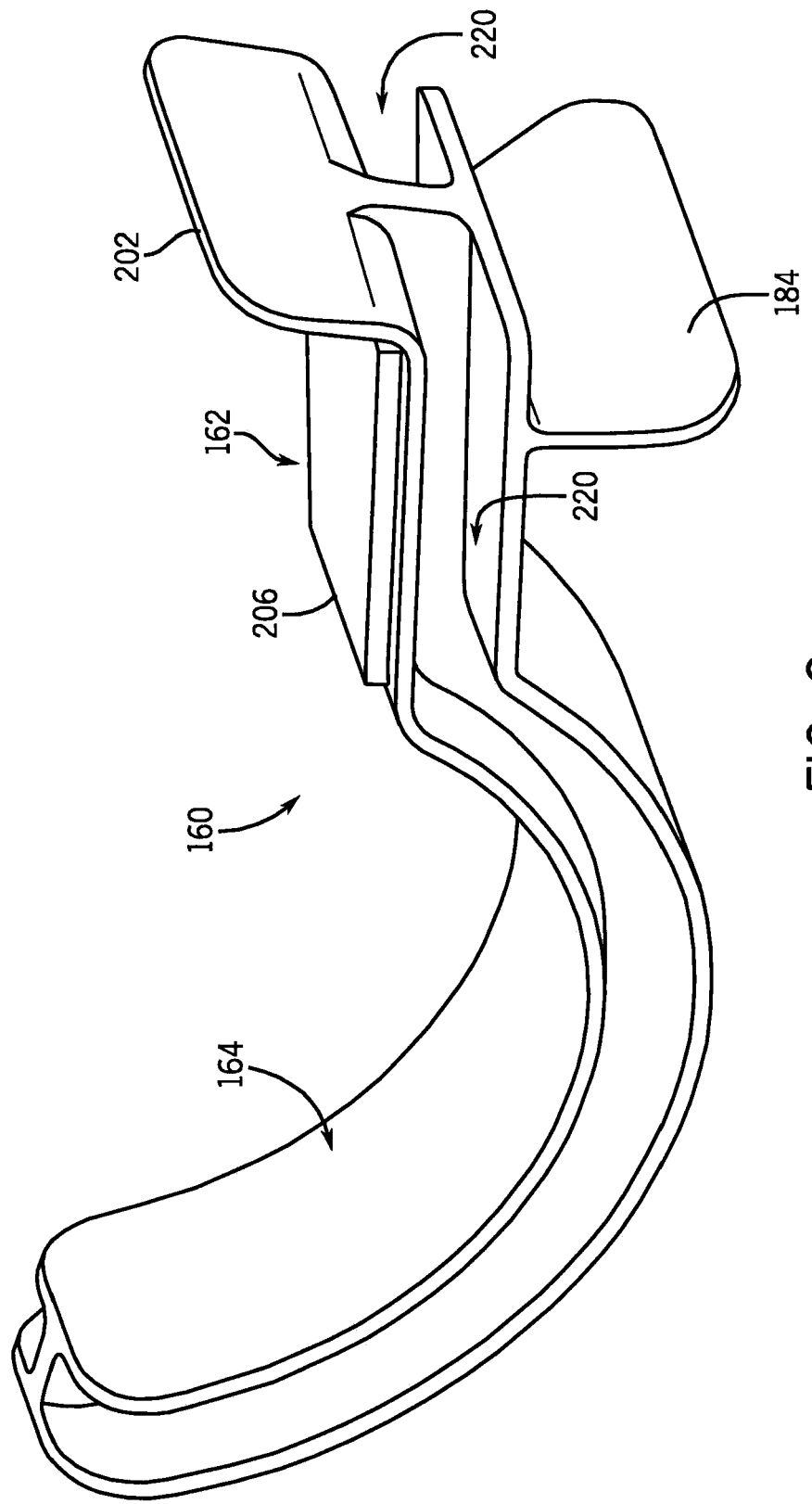
FIG. 9 is a perspective view of the oropharyngeal airway of FIG. 8 viewed from a different angle than FIG. 8.
Figure 10:
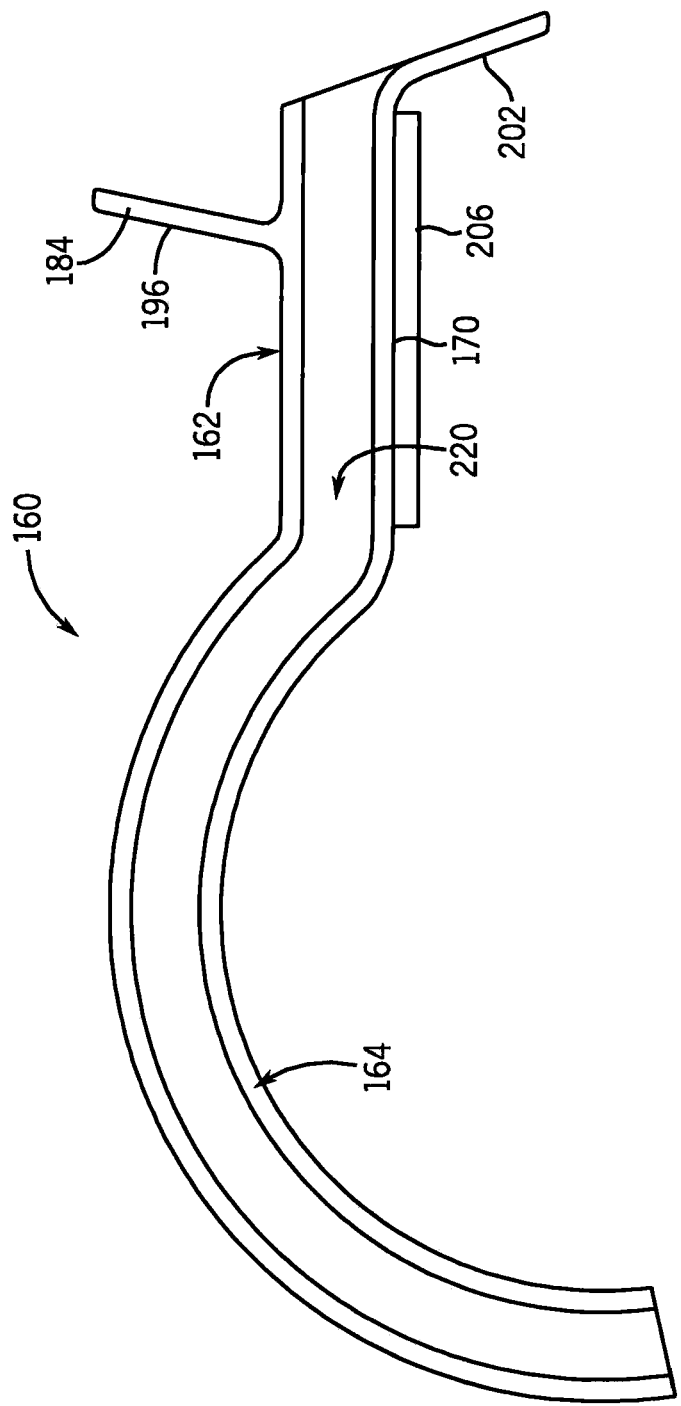
FIG. 10 is a side elevation view of the oropharyngeal airway of FIG. 8.
Figure 11:
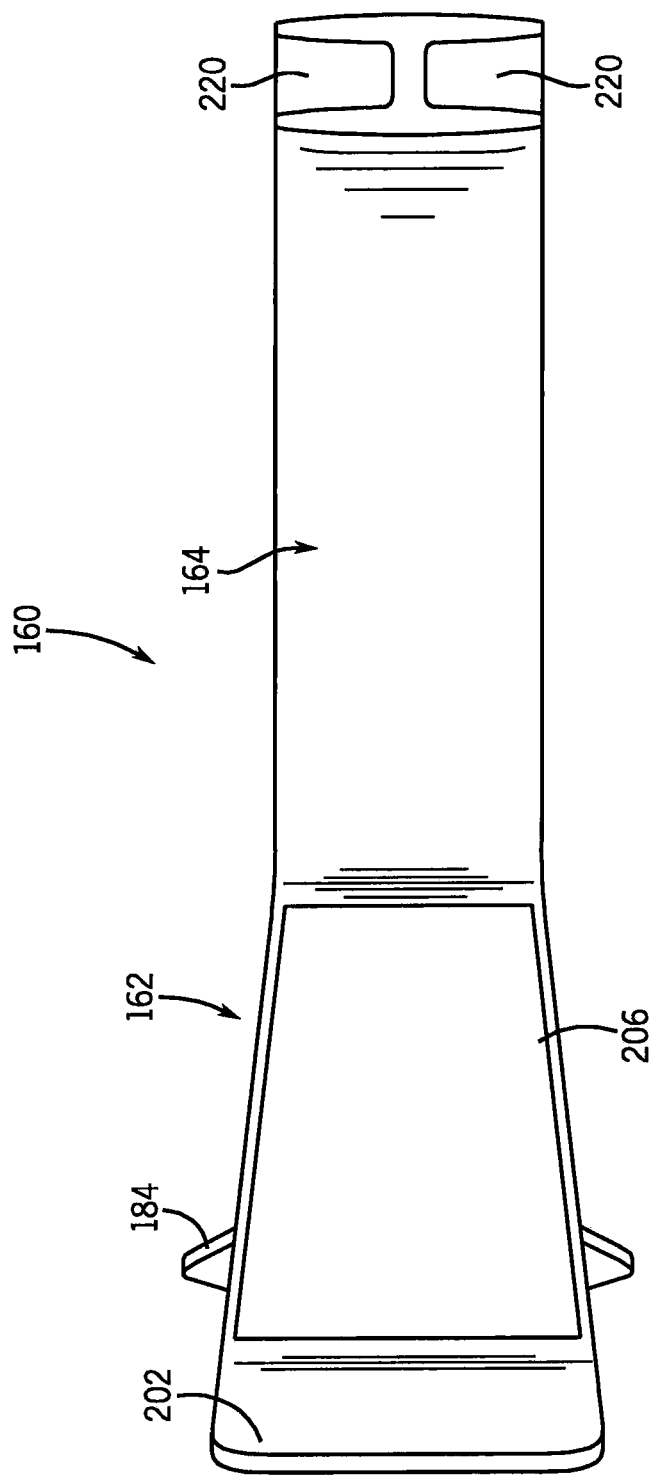
FIG. 11 is an anterior view of the oropharyngeal airway of FIG. 8.

As most easily seen in FIGS. 3, 6, and 7, the maxillary flange 84 preferably has a width greater than the width of the bite block 66. Such a width of the maxillary flange 84 is preferably provided by an outward taper from a proximal end 88 that connects to the bite block 66 to a distal end 90 opposite the proximal end 88. In addition, lateral side surfaces 92 and 94 of the maxillary flange 84 are preferably angled toward the pharyngeal section 64 to provide a concave proximal surface 96 and a convex distal surface 98. The concave proximal surface 96 closely matches the shape of the maxilla, and the lateral side surfaces 92 and 94 of the convex distal surface 98 effectively accommodate the thumbs of the practitioner to stabilize the device when applying a jaw thrust as described below.

Referring again to FIGS. 2-7, a mandibular section 100 of the proximal section 62 includes the mandibular surface 70 and a mandibular flange 102 adjacent the mandibular surface 70. In some situations, the mandibular flange 102 prevents the patient's lower lip from obstructing the internal channel 80. The mandibular flange 102, which preferably has a flat shape, unlike the maxillary flange 84, extends outwardly and generally away from the pharyngeal section 64 at an angle β relative to the longitudinal axis 86. The angle β is preferably in the range of 45 to 80 degrees, and is most preferably about 60 degrees. In addition, the mandibular flange 102 extends outwardly from the bite block 66 at a position adjacent the distal end 78. As a result and as most clearly shown in FIG. 4, the mandibular flange 102 and the distal end 78 may define a common distal surface 104 oriented at the angle β relative to the longitudinal axis 86.

The mandibular surface 70 of the mandibular section 100 is longer than the proximate maxillary surface 68 in the direction of the longitudinal axis 86 to permit a portion of the mandibular surface 70 opposite the maxillary flange 84 to engage at least a portion of the mandible, which should be understood to mean one or more lower teeth, and/or the lower gums. A ratio of the length of the mandibular surface 70 to the length of the proximate maxillary surface 68 may be, for example, 5:4 or greater. Such a ratio provides the bite block 66 with a generally asymmetric shape over a plane parallel to the mandibular surface 70 and the maxillary surface 68. In addition, the mandibular surface 70 preferably supports a generally deformable block or pad 106, such as pad comprising an elastomeric foam material or the like. As shown in the figures, the pad 106 may have a three-dimensional trapezoid shape, although other shapes are also possible. Furthermore, the pad 106 may be adhesively connected to the mandibular surface 70, although other methods may also be used. In any case, the pad 106 atraumatically provides increased adherence to prevent the lower teeth 16 from sliding or otherwise moving over the bite block 66.

Still referring to FIGS. 2-7, the pharyngeal section 64 generally has the same shape as previous oropharyngeal airway designs. That is, the pharyngeal section 64 has curved shape that generally matches the shape of the patient's tongue. The pharyngeal section 64 extends from a proximal end 108 that connects to the proximal section 62 to a distal end 110 opposite the proximal section 62. Referring specifically to FIG. 5, the pharyngeal section 64 partially defines the internal channel 80 and may have a hollow cross-sectional shape that includes portions of a rectangle and a circle. Alternatively, the pharyngeal section 64 may have circular, oval, or any other cross-sectional shape that appropriately engages the tissues within the mouth and throat.

The pharyngeal section and the proximal section may have non-hollow cross-sectional shapes without departing from the scope of the invention. For example, in a second embodiment shown in FIGS. 8-11, the device 160 includes a pharyngeal section 164 and a proximal section 162 that have I-shaped cross-sections to provide external channels 220 instead of the internal channel 80 (FIGS. 2-7). The proximal surface 196 is preferably flat in the second embodiment to provide a device that easier to form in a molding process than a device with a concave proximal surface 96 (FIGS. 2-7). Other components of the device 160, such as the maxillary flange 184 and the mandibular flange 202, are otherwise as described above. The mandibular surface 170 may support a generally deformable block or pad 206 as described above.

Figure 12:
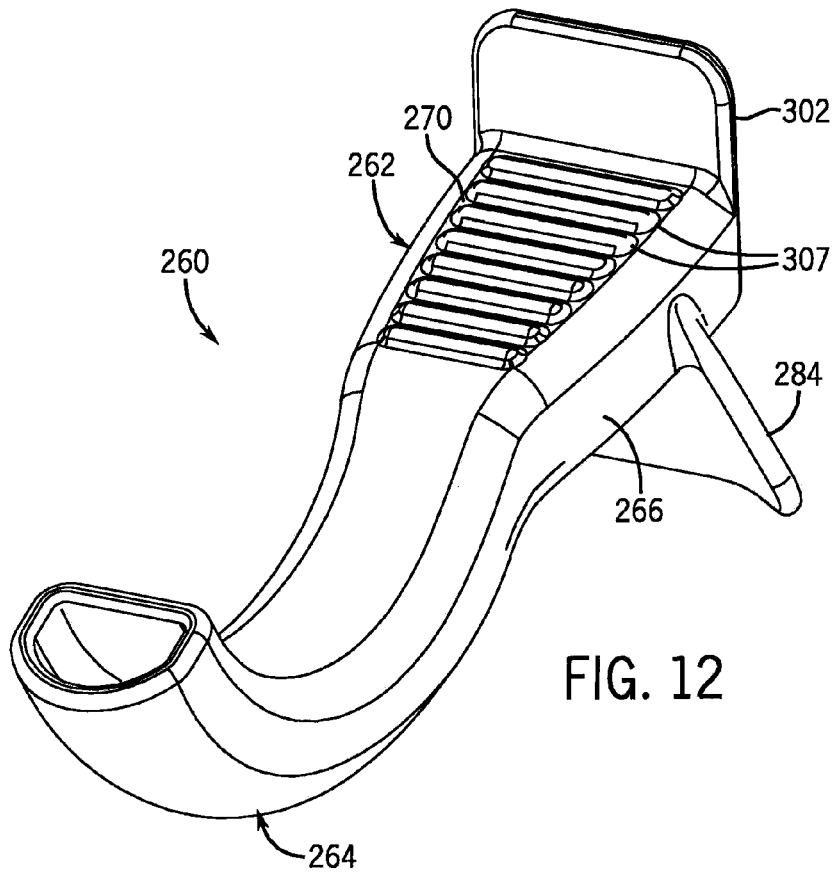
FIG. 12 is a perspective view of a third embodiment of an oropharyngeal airway of the present invention.
Figure 13:
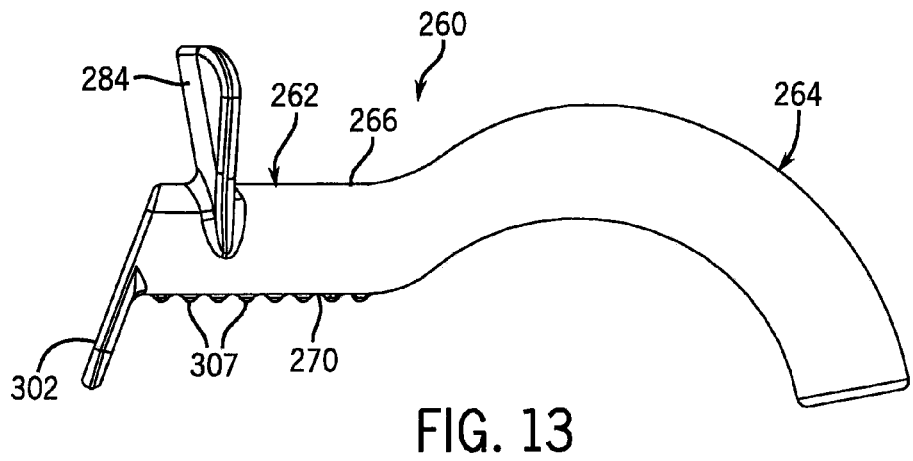
FIG. 13 is a perspective view of the oropharyngeal airway of FIG. 12 viewed from a different angle than FIG. 12.

Referring now to FIGS. 12 and 13, a third embodiment of the device 260 includes a pharyngeal section 264 and as described above in connection with the first embodiment of the device 60. The device 260 also includes a proximal section 262 having maxillary and mandibular flanges 284 and 302 as described above. Unlike the previous embodiments, the mandibular surface 270 of the device 260 is generally rough to provide increased adherence and prevent the lower teeth 16 from sliding or otherwise moving over the bite block 266. The mandibular surface 270 may be rough due to multiple ridges 307 that extend in the width direction of the device 260, small dimples, or the like.

The aforementioned features and shapes of the oropharyngeal airway 60, for example, the length of the mandibular section 100 relative to the proximate maxillary surface 68, or the portion of the mandibular section 100 opposite the maxillary flange 84, advantageously permit the oropharyngeal airway 60 to be used with recommended ventilation techniques and/or a face mask. Use of the oropharyngeal airway 60 with recommended ventilation techniques and/or a face mask is described in further detail below. The oropharyngeal airways 160 and 206 may also be used as described below, although only the airway 60 and its features are referenced for simplicity.

Figure 14:
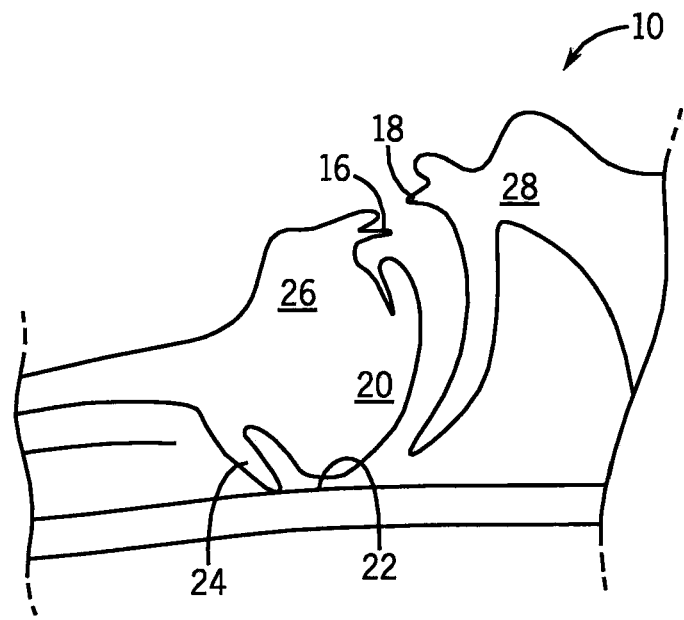
FIG. 14 is a side elevation view of an unconscious patient illustrating a relaxed position of the mandible and an airway obstruction.
Figure 16:
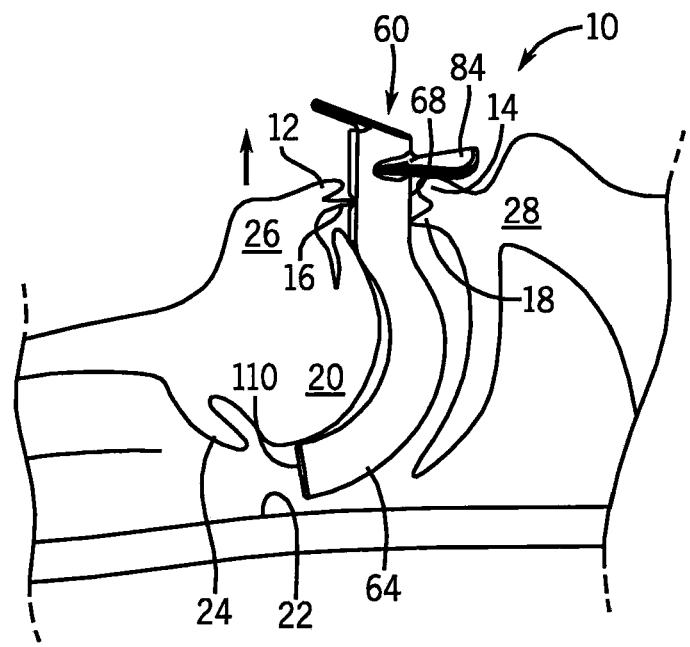
FIG. 16 is a side elevation view of the oropharyngeal airway of FIG. 2 in a patient's mouth after applying a jaw thrust maneuver.

One or more practitioners use the oropharyngeal airway 60, preferably in addition to other devices, to ventilate an unconscious patient. Referring to FIG. 14, before ventilating the unconscious patient 10, the mandible 26 may have relaxed and moved to a posterior position in contrast to a normal position relative to the maxilla 28. As a result, contact of the throat soft tissues, such as the tongue 20, the pharynx 22, and the epiglottis 24, may have obstructed the airway of the patient 10. Referring now to FIG. 16, the practitioner first inserts the oropharyngeal airway 60 into the mouth and throat of the patient 10 such that several features of the oropharyngeal airway 60 engage parts of the patient's head. For example, the proximate maxillary surface 68 preferably engages one or more of the upper teeth 18. The maxillary flange 84 preferably engages at least a portion of the maxilla 28, which should be understood to mean the upper lip 14 and/or one or more upper teeth 18, to stabilize the oropharyngeal airway 60. In addition, the pharyngeal section 64 engages the tongue 20.

Figure 15:
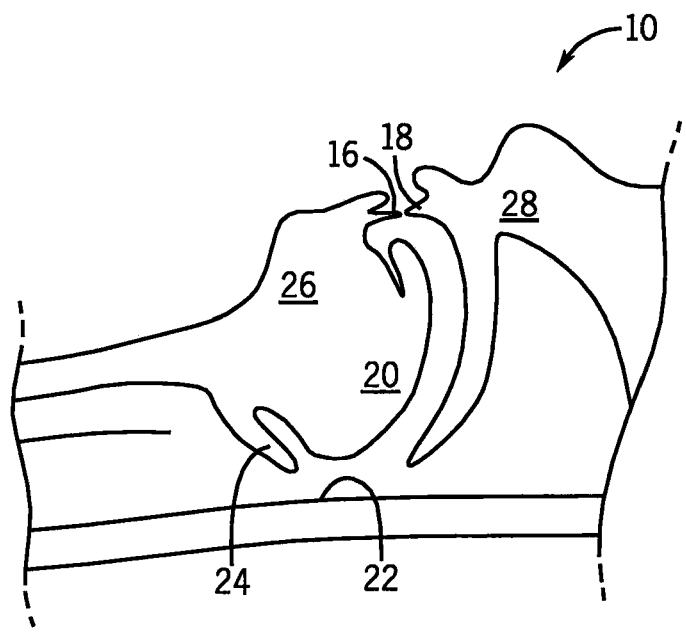
FIG. 15 is a side elevation view of a patient illustrating a normal position of the mandible.

The practitioner next applies a jaw thrust maneuver to advance the mandible 26 of the patient. With the exception of the oropharyngeal airway 60 being in the patient's mouth, the jaw thrust maneuver is preferably performed as described in Basic Life Support for Health Care Providers and the Guidelines 2003 for Cardiopulmonary Resuscitation and Emergency Cardiovascular Care, incorporated herein by reference as if set forth in its entirety. The jaw thrust maneuver moves the mandible 26 to a prognathic position as shown in FIG. 16. In the prognathic position, the mandible 26 is anterior relative to its normal position (FIG. 15) and preferably at least a portion of the mandible 26, which should be understood to mean the lower lip 12, one or more lower teeth 16, and/or the lower gums, is anterior relative to at least a portion of the upper teeth 18. Next, the mandible 26 is held in the prognathic position by engaging at least a portion of the mandible 26 against the mandibular surface 70 of the device 60. The mouth is also held in an open position due to the oropharyngeal airway 60.

Figure 17:
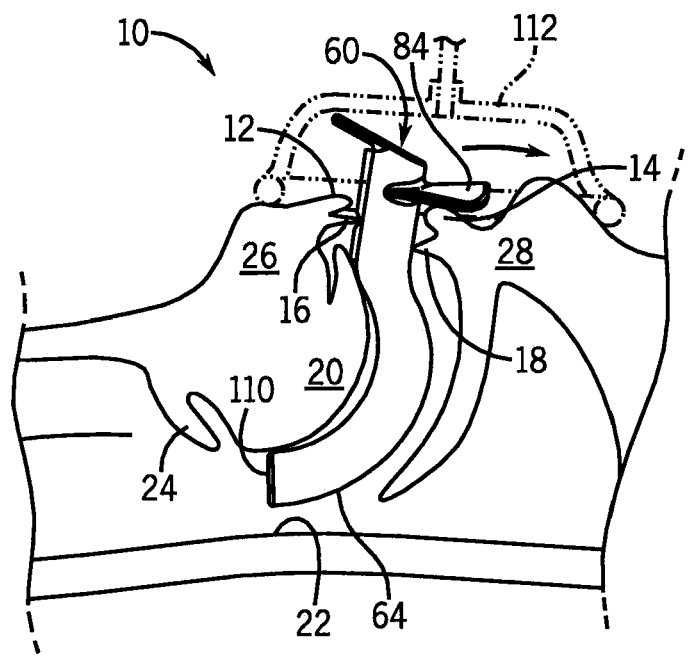
FIG. 17 is a side elevation view of the oropharyngeal airway of FIG. 2 in a patient's mouth after applying a head extension maneuver.

Referring now to FIG. 17, the practitioner next preferably applies a ventilation face mask 112 against the face and over the mouth of the patient 10. The ventilation face mask 112, if used, is preferably the ergonomic face mask described in U.S. Pat. No. 6,651,661, the disclosure of which is hereby incorporated by reference in its entirety. The practitioner next preferably holds the ventilation face mask 112 over the mouth of the patient and applies chin lift grip that maintains the mandible in the prognathic position and a head extension maneuver as described in U.S. Pat. No. 6,651,661. However, unlike previous practices, the head extension maneuver may be applied using only a single hand because the oropharyngeal airway 60 holds the mouth open and holds the mandible 26 in the prognathic position. The head extension maneuver, which completes the triple airway maneuver by following the jaw thrust maneuver and opening of the mouth, relieves obstruction between the tongue 20 and the pharynx 22 and most importantly between the epiglottis 24 and the pharynx 22 beyond the distal end 110 of the oropharyngeal airway 60. In addition, during the head extension maneuver, the prognathic position of the mandible 26 causes the teeth 16 and 18, or in some cases, the gums, to apply a torque on the oropharyngeal airway 60 such that the distal end 110 is elevated. Elevation of the distal end 110 moves the tongue 20 and the epiglottis 24 further above the pharynx 22.

Still referring to FIG. 17, the practitioner holds the patient in the ventilation position after the triple airway maneuver is performed. Unlike previous practices, the patient may be held in the ventilation position using only a single hand because the other hand of the practitioner is not needed to hold the mandible 26 in the prognathic position. The single hand is preferably the hand that holds the ventilation face mask 112 against the face of the patient 10. The other hand may be used to compress a medical resuscitator bag, such as a well-known autoinflatable "bag" that connects to the ventilation face mask 112, to ventilate the patient 10. As a result, the oropharyngeal airway 60 permits a single practitioner to perform the triple airway maneuver and subsequently ventilate the patient 10. The oropharyngeal airway 60 may also be used when two practitioners are available to further ensure the patient 10 is properly ventilated. Specifically, one of the practitioners may use two hands to apply the triple airway maneuver and hold the patient in the ventilation position and the other practitioner may compress the resuscitator bag.

It should be apparent from the previous paragraphs and the figures that the longer length of the mandibular surface 70 compared to the proximate maxillary surface 68 permit the jaw thrust maneuver to be applied after the oropharyngeal airway 60 is inserted into the mouth and throat of the patient 10. As a result, the lengths of the mandibular and maxillary surfaces 70 and 68 also permit the triple airway maneuver to be performed after the oropharyngeal airway 60 is in position. Further still, the lengths of the surfaces 70 and 68 permit the mandible 26 to be positioned so that the teeth 16 and 18 apply a torque on the oropharyngeal airway 60 such that the distal end 110 is elevated.

As briefly described above, the oropharyngeal airway 60 may also be used in other situations in which mandibular advancement is advantageous for patient care. For example, the oropharyngeal airway 60 may be used as a fiber optic oropharyngeal airway, a resuscitation mouthpiece, or the like.

It is specifically intended that the present invention not be limited to the embodiments and illustrations contained herein, but include modified forms of those embodiments including portions of the embodiments and combinations of elements of different embodiments as come within the scope of the following claims.

I claim:

1. An oropharyngeal device for assisting oral ventilation of a patient, comprising:

a pharyngeal section configured to engage the tongue of the patient;

a bite block connected to the pharyngeal section, the bite block defining a channel, a direction in which air flows through the channel defining a longitudinal axis direction, and the bite block including:

a proximate maxillary surface configured to engage at least a portion of the maxilla of the patient;

a maxillary flange adjacent the proximate maxillary surface, and the maxillary flange being configured to engage the upper lip of the patient;

a mandibular surface opposite the proximate maxillary surface, and at least a portion of the mandibular surface opposite the maxillary flange being configured to engage at least a portion of the mandible of the patient; and a mandibular flange adjacent the mandibular surface, separate from and not in contact with the maxillary flange, and offset from the maxillary flange in the longitudinal axis direction.

2. The oropharyngeal device of claim 1, wherein a length of the mandibular surface in the longitudinal axis direction is greater than a length of the proximate maxillary surface in the longitudinal axis direction.

3. The oropharyngeal device of claim 2, wherein a ratio of the length of the mandibular surface in the longitudinal axis direction to the length of the proximate maxillary surface in the longitudinal axis direction is at least 5:4 to provide the bite block with a generally asymmetric shape.

4. The oropharyngeal device of claim 1, further comprising first and second lateral side surfaces connecting the proximate maxillary surface and the mandibular surface, and wherein the first and second lateral side surfaces taper outwardly to provide the proximate maxillary surface and the mandibular surface with generally trapezoidal shapes.

5. The oropharyngeal device of claim 1, wherein at least one of a first angle from the longitudinal axis direction to the maxillary flange is less than 90 degrees and a second angle from the longitudinal axis direction to the mandibular flange is less than 90 degrees.

6. An oropharyngeal device for assisting oral ventilation of a patient, comprising:

a pharyngeal section configured to engage the tongue of the patient;

a bite block connected to the pharyngeal section, the bite block including:

a channel, a direction in which air flows through the channel defining a longitudinal axis, a distal end opposite the pharyngeal portion;

a maxillary flange offset from the distal end towards the pharyngeal section, the maxillary flange being configured to engage the upper lip of the patient, and the maxillary flange including;
    a proximal surface generally facing the pharyngeal portion;
    a maxillary distal surface generally facing away from the pharyngeal portion;
a mandibular surface configured to engage at least a portion of the mandible of the patient;
a mandibular flange adjacent the mandibular surface and including a mandibular distal surface generally facing away from the pharyngeal portion;
a proximate maxillary surface opposite the mandibular surface and adjacent the proximal surface of the maxillary flange, and the proximate maxillary surface being configured to engage at least a portion of the maxilla of the patient; and
wherein a first angle from a portion of the longitudinal axis adjacent the distal end to the maxillary distal surface is less than 90 degrees and a second angle from a portion of the longitudinal axis adjacent the distal end to the mandibular distal surface is less than 90 degrees.

7. The oropharyngeal device of claim 6, wherein the first angle is in the range of about 75 to 80 degrees.

8. The oropharyngeal device of claim 6, wherein the mandibular surface supports a deformable pad.

9. The oropharyngeal device of claim 6, further comprising first and second lateral side surfaces connecting the proximate maxillary surface and the mandibular surface, and wherein the first and second lateral side surfaces taper outwardly to provide the proximate maxillary surface and the mandibular surface with generally trapezoidal shapes.

10. The oropharyngeal device of claim 6, wherein the second angle is in the range of about 45 to 80 degrees.

11. The oropharyngeal device of claim 10, wherein the first angle is in the range of about 75 to 80 degrees.

12. The oropharyngeal device of claim 6, wherein the mandibular flange is offset from the maxillary flange along the longitudinal axis.

13. A method of treating a patient in a supine position, comprising the steps of:
inserting an oropharyngeal device into the throat of the patient, the oropharyngeal device comprising:
    a proximate maxillary surface;
    a maxillary flange adjacent the proximate maxillary surface;
    a mandibular surface opposite the proximate maxillary surface, and at least a portion of the mandibular surface opposite the maxillary flange;
    a pharyngeal section adjacent the proximate maxillary surface and the mandibular surface;
engaging the pharyngeal section with the tongue of the patient;
engaging the maxillary flange with at least a portion of the maxilla of the patient;
while the oropharyngeal device is disposed in the throat of the patient, the pharyngeal section is engaged with the tongue of the patient, and the maxillary flange is engaged with the portion of the maxilla of the patient, performing the steps of:
i. applying a jaw thrust maneuver to advance the mandible of the patient to a prognathic position past a normal position of the mandible relative to the maxilla;
ii. maintaining the mouth of the patient in an open position after applying the jaw thrust maneuver;
iii. holding the mandible in the prognathic position by engaging at least a portion of the mandible with the portion of the mandibular surface opposite the maxillary flange after applying the jaw thrust maneuver; and
iv. applying a head extension maneuver to rotate the head of the patient after applying the jaw thrust maneuver.

14. The method of claim 13, further comprising the step of positioning a ventilation mask against the face of the patient after applying the jaw thrust maneuver.

15. The method of claim 14, wherein the step of applying the head extension maneuver to rotate the head of the patient is performed after positioning the ventilation mask.

16. The method of claim 15, wherein the ventilation mask is held against the face and the patient is held in a ventilation position after applying the head extension maneuver by only a single practitioner using only a single hand.

17. The method of claim 15, further comprising the step of ventilating the patient by compressing a resuscitator bag connected to the ventilation mask after applying the head extension maneuver.

18. The method of claim 17, wherein the ventilation mask is held against the face and the patient is held in a ventilation position after applying the head extension maneuver by only a single practitioner using only a first hand, and wherein the resuscitator bag is compressed by the single practitioner using only a second hand.

19. The method of claim 13, wherein at least a portion of the mandible is positioned anterior relative to at least a portion of the maxillary flange after applying the jaw thrust maneuver.

20. The method of claim 13, further comprising the step of positioning the mandible relative to the maxilla to lift the pharyngeal section of the oropharyngeal device and thereby relieve an obstruction proximate the epiglottis of the patient.

21. An oropharyngeal device for assisting oral ventilation of a patient, comprising:
a pharyngeal section configured to engage the tongue of the patient;
a bite block connected to the pharyngeal section, the bite block defining a channel, a direction in which air flows through the channel defining a longitudinal axis direction, and the bite block including:
    a proximate maxillary surface configured to engage at least a portion of the maxilla of the patient;
    a maxillary flange adjacent the proximate maxillary surface, and the maxillary flange being configured to engage the upper lip of the patient;
    a mandibular surface opposite the proximate maxillary surface, and at least a portion of the mandibular surface opposite the maxillary flange being configured to engage at least a portion of the mandible of the patient; and
    a mandibular flange adjacent the mandibular surface and offset from the maxillary flange in the longitudinal axis direction,
wherein a length of the mandibular surface in the longitudinal axis direction is greater than a length of the proximate maxillary surface in the longitudinal axis direction, and
wherein a ratio of the length of the mandibular surface in the longitudinal axis direction to the length of the proximate maxillary surface in the longitudinal axis direction is at least 5:4 to provide the bite block with a generally asymmetric shape.

22. An oropharyngeal device for assisting oral ventilation of a patient, comprising:

a pharyngeal section configured to engage the tongue of the patient;
a bite block connected to the pharyngeal section, the bite block defining a channel, a direction in which air flows through the channel defining a longitudinal axis direction, and the bite block including:
 a proximate maxillary surface configured to engage at least a portion of the maxilla of the patient;
 a maxillary flange adjacent the proximate maxillary surface, and the maxillary flange being configured to engage the upper lip of the patient;
 a mandibular surface opposite the proximate maxillary surface, and at least a portion of the mandibular surface opposite the maxillary flange being configured to engage at least a portion of the mandible of the patient;
 a mandibular flange adjacent the mandibular surface and offset from the maxillary flange in the longitudinal axis direction; and
 first and second lateral side surfaces connecting the proximate maxillary surface and the mandibular surface,
 wherein the first and second lateral side surfaces taper outwardly to provide the proximate maxillary surface and the mandibular surface with generally trapezoidal shapes.

23. An oropharyngeal device for assisting oral ventilation of a patient, comprising:
a pharyngeal section configured to engage the tongue of the patient;
a bite block connected to the pharyngeal section, the bite block including:
 a channel, a direction in which air flows through the channel defining a longitudinal axis,
 a distal end opposite the pharyngeal portion;
 a maxillary flange offset from the distal end towards the pharyngeal section, the maxillary flange being configured to engage the upper lip of the patient, and the maxillary flange including;
  a proximal surface generally facing the pharyngeal portion;
  a maxillary distal surface generally facing away from the pharyngeal portion;
 a mandibular surface configured to engage at least a portion of the mandible of the patient;
 a mandibular flange adjacent the mandibular surface and including a mandibular distal surface generally facing away from the pharyngeal portion; and
 a proximate maxillary surface opposite the mandibular surface and adjacent the proximal surface of the maxillary flange, and the proximate maxillary surface being configured to engage at least a portion of the maxilla of the patient,
wherein at least one of a first angle from a portion of the longitudinal axis adjacent the distal end to the maxillary distal surface is less than 90 degrees and a second angle from a portion of the longitudinal axis adjacent the distal end to the mandibular distal surface is less than 90 degrees,
wherein first and second lateral side surfaces connect the proximate maxillary surface and the mandibular surface, and
wherein the first and second lateral side surfaces taper outwardly to provide the proximate maxillary surface and the mandibular surface with generally trapezoidal shapes.

* * * * *